(12) United States Patent
Lee et al.

(10) Patent No.: US 11,524,935 B2
(45) Date of Patent: *Dec. 13, 2022

(54) METHODS FOR TREATING ATTENTION-DEFICIT/HYPERACTIVITY DISORDER

(71) Applicant: SK Biopharmaceuticals Co., Ltd., Seongnam-si (KR)

(72) Inventors: Sung James Lee, Montville, NJ (US); Susan Marie Melnick, Parsippany, NJ (US)

(73) Assignee: SK Biopharmaceuticals Co., Ltd., Seongnam-si (KR)

( * ) Notice: Subject to any disclaimer, the term of this patent is extended or adjusted under 35 U.S.C. 154(b) by 34 days.

This patent is subject to a terminal disclaimer.

(21) Appl. No.: 17/029,151

(22) Filed: Sep. 23, 2020

(65) Prior Publication Data

US 2021/0070694 A1  Mar. 11, 2021

Related U.S. Application Data

(63) Continuation of application No. 16/225,893, filed on Dec. 19, 2018, now abandoned, which is a continuation of application No. 15/605,278, filed on May 25, 2017, now Pat. No. 10,202,335, which is a continuation of application No. 14/495,532, filed on Sep. 24, 2014, now Pat. No. 9,663,455, which is a continuation of application No. 13/508,147, filed as application No. PCT/KR2010/007698 on Nov. 3, 2010, now Pat. No. 8,895,609.

(60) Provisional application No. 61/258,780, filed on Nov. 6, 2009.

(51) Int. Cl.
C07C 271/12 (2006.01)
A61K 31/27 (2006.01)

(52) U.S. Cl.
CPC ............ *C07C 271/12* (2013.01); *A61K 31/27* (2013.01)

(58) Field of Classification Search
CPC .......... A61K 31/27; A61P 25/00; A61P 25/14; C07C 271/12
See application file for complete search history.

(56) References Cited

U.S. PATENT DOCUMENTS

| | | | |
|---|---|---|---|
| 5,705,640 A | 1/1998 | Choi et al. |
| 5,756,817 A | 5/1998 | Choi et al. |
| 5,955,499 A | 9/1999 | Choi et al. |
| 6,002,009 A | 12/1999 | Cereda et al. |
| 6,140,532 A | 10/2000 | Choi et al. |
| 7,642,261 B2 | 1/2010 | Bartoszyk et al. |
| 8,232,315 B2 | 7/2012 | Lee et al. |
| 8,304,431 B2 | 11/2012 | Buntinx |
| 8,552,060 B2 | 10/2013 | Palumbo et al. |
| 8,623,913 B2 | 1/2014 | Melnick et al. |
| 8,895,609 B2 | 11/2014 | Lee et al. |
| 2001/0034320 A1 | 10/2001 | Brecht et al. |
| 2002/0151585 A1 | 10/2002 | Plata-Salaman et al. |
| 2002/0156127 A1 | 10/2002 | Plata-Salaman et al. |
| 2003/0153612 A1 | 8/2003 | Sethi |
| 2003/0187021 A1 | 10/2003 | Edgar et al. |
| 2004/0115263 A1 | 6/2004 | Robertson et al. |
| 2005/0080268 A1 | 4/2005 | Choi et al. |
| 2006/0258718 A1 | 11/2006 | Choi et al. |
| 2007/0123519 A1 | 5/2007 | Choi et al. |
| 2007/0197657 A1 | 8/2007 | Beyreuther et al. |
| 2007/0276047 A1 | 11/2007 | Oberegger et al. |
| 2008/0031932 A1 | 2/2008 | Midha |
| 2008/0039529 A1 | 2/2008 | Sporn |
| 2008/0090902 A1 | 4/2008 | Pandey et al. |
| 2010/0093801 A1 | 4/2010 | Chung et al. |
| 2012/0245226 A1 | 9/2012 | Lee et al. |
| 2012/0252892 A1 | 10/2012 | Lee et al. |
| 2013/0137764 A1 | 5/2013 | Ahnaou et al. |

FOREIGN PATENT DOCUMENTS

| | | |
|---|---|---|
| EP | 0633023 | 1/1995 |
| JP | 2007513095 | 5/2007 |
| JP | 2008518921 | 6/2008 |
| JP | 2008545795 | 12/2008 |
| JP | 2008546778 | 12/2008 |
| JP | 5836280 | 12/2015 |
| WO | 9607637 | 3/1996 |
| WO | 9624577 | 8/1996 |
| WO | 9632375 | 10/1996 |
| WO | 9815526 | 4/1998 |
| WO | 98017636 | 4/1998 |
| WO | 9902494 | 1/1999 |
| WO | 9921561 | 5/1999 |
| WO | 9955674 | 11/1999 |
| WO | 0250071 | 6/2002 |
| WO | 02080928 | 10/2002 |
| WO | 02100352 | 12/2002 |
| WO | 2004026868 | 4/2004 |

(Continued)

OTHER PUBLICATIONS

"Office Action corresponding to Brazilian Application No. 112012010670-8 dated Jun. 17, 2021".
"The Merck Manual of Diagnosis and Therapy", Seventeenth edition, Merck Research Laboratories, p. 2255-2258 (Jan. 1999).
"Daughton & Kratochvil, Review of ADHD Pharmacotherapies: Advantages, Disadvantages, and Clinical Pearls, J. Am. Acad. Child Adolesc. Psychiatry, 48:3, 240-248, Mar. 2009".
"U.S. Appl. No. 12/827,529; Office Action dated Apr. 22, 2013".
"U.S. Appl. No. 13/508,145; Office Action dated Apr. 15, 2013".
"Belikov V.G., Pharmaceutical Chem. M. Vysshaya Shkola p. 43-47 (1993)".

(Continued)

*Primary Examiner* — Umamaheswari Ramachandran
(74) *Attorney, Agent, or Firm* — Myers Bigel, P.A.

(57) ABSTRACT

The invention is directed to a method of treating attention-deficit/hyperactivity disorder (ADHD) in a subject, comprising administering a therapeutically effective amount of a carbamoyl compound, or pharmaceutically acceptable salt thereof.

16 Claims, 5 Drawing Sheets

(56) References Cited

FOREIGN PATENT DOCUMENTS

| WO | 2004094418 | 11/2004 |
|---|---|---|
| WO | 2005021539 | 3/2005 |
| WO | 2005092882 | 10/2005 |
| WO | 2006050037 | 5/2006 |
| WO | 2006106425 | 10/2006 |
| WO | 2006133393 | 12/2006 |
| WO | 2007018496 | 2/2007 |
| WO | 2008048801 | 4/2008 |
| WO | 2008067060 | 6/2008 |
| WO | 2011005473 | 1/2011 |

OTHER PUBLICATIONS

"Bennett, Clinical Manifestations and Diagnosis of Fibromyalgia," Rhuem Dis Clin N Am, 2009, vol. 35, pp. 215-232.
"Daley, Update on attention-deficit/hyperactivity disorder, Current Opinion in Pediatrics, 16:217-226, 2004".
"European Search Report for Application No. 10828479.5 dated Mar. 27, 2013".
"European Search Report for Application No. 10828500.8 dated Mar. 12, 2013".
"Ferini-Strambi. Treatment Options for Restless Legs Syndrome", Expert Opin. Pharmacother., vol. 10, No. 4, pp. 545-554, 2009.
"Henningfield, Nicotine Medications for Smoking Cessation," The New England Journal of Medicine, Nov. 2, 1995, vol. 333, No. 18, pp. 1196-1203.
"Hornyak Depressive Disorders in Restless Legs Syndrome", CNS Drugs, vol. 24, No. 2, pp. 89-98, 2010.
"International Preliminary Report on Patentability corresponding to International Application No. PCT/KR2011/004677 dated Jan. 17, 2013".
"International Search Report and Written Opinion corresponding to International Application No. PCT/KR2009/005863 dated May 28, 2010".
"International Search Report, and Written Opinion corresponding to International Application No. PCT/KR2010/007603 dated Jul. 29, 2011".
"International Search Report and Written Opinion corresponding to International Application No. PCT/KR2010/007698 dated Jul. 22, 2011".
"International Search Report corresponding to International Application No. PCT/KR2011/004677 dated Feb. 24, 2012".
"J. G. Cannon Chapter Nineteen in Burger's Medicinal Chemistry and Drug Discovery, Fifth Edition, vol. I Principles and Practice, Wiley-Interscience 1995, pp. 783-802, 784).".
"MEASE, Fibromyalgia Syndrome: Review of Clinical Presentation, Pathogenesis, Outcome Measures, and Treatment," The Journal of Rheumatology, 2005, vol. 32, Suppl. 75, pp. 6-21.
"Murphy & Adler, J Clin Psychiatry 2004; 65:12-17, 2004".
"Office Action corresponding to Australian Application No. 2010316106 dated Oct. 23, 2014".
"Office Action corresponding to Japanese Application No. 2015-134626 dated Jul. 6, 2016".
"Office Action corresponding to Russian Application No. 2012123155/15(035223) dated Aug. 15, 2014.".
"ONDO, Restless Legs Syndrome", Neurol Clin, vol. 27, pp. 779-799, 2009.
"Phenprobamate, Wikipedia, https://en.wikipedia.org/wiki/Phenprobamate, last edited Apr. 2, 2016, accessed Sep. 24, 2019".
"RAO, Recent Developments of Collagen-Based Materials for Medical Applications and Drug Delivery Systems", J. Biomater. Sci. Polymer Edn., vol. 7, No. 7, pp. 623-645, 1995.
"TJWA, Budesonide Inhaled Via Turbuhaler: A More Effective Treatment for Asthma than Beclomethasone Dipropionate Via Rota haler", Annals of Allergy, Asthma, & Immunology, vol. 75, pp. 107-111, 1995.
Allen , et al., "MRI Measurement of Brain Iron in Patients with Restless Legs Syndrome", Neurology, vol. 56, pp. 263-265, Jan. 2001.
Al-Muhammed , et al., "In-Vivo Studies on Dexamethasone Sodium Phosphate Liposomes", J. Microencapsulation, vol. 13, No. 3, pp. 293-306, 1996.
Amsterdam Jay D. , et al., "A single-site, double-blind, placebo-controlled, dose-ranging study of YKP10A: A putative, new antidepressant", Progress in Neuro-Psychopharmacology & Biological Psychiatry, Dec. 1, 2002, pp. 1333-1338.
Arnold , et al., "Comorbidity of Fibromyalgia and Psychiatric Disorders," J Clin Psychiatry, Aug. 2006, vol. 67, No. 8, pp. 1219-1225.
Azorin , et al., "An Update on the Treatment of Bipolar Depression", Expert Opin. Pharmacother., vol. 10, No. 2, pp. 161-172, 2009.
"Banno , et al., Sleep Medicine (2000) pp. 221-229".
Bayard , et al., "Restless Legs Syndrome", American Family Physician, vol. 73, No. 2, pp. 235-240, Jul. 15, 2008.
Beers, M. , et al., "The Merck Manual of Diagnosis and Therapy" Merck Research Laboratories, Mar. 5, 1999, seventeenth edition, pp. 2254-2259.
Bennett , et al., "A peripheral mononeuropathy in rat that produces disorders of pain sensation like those seen in man," Pain, 1988, vol. 33, pp. 87-107.
"Cam I , et al., The New England Journal of Medicine (2003) Massachusetts Medical Society, vol. 349, pp. 975-986".
Chengappa , et al., "Barriers to the Effective Management of Bipolar Disorder: A Survey of Psychiatrists Based in the UK and USA", Bipolar Disorders, vol. 7, suppl.1, pp. 38-42, 2005.
"Chonn , et al., Recent Advances in Liposomal Drug-Delivery Systems", Current Opinion in Biotechnology, vol. 6, pp. 698-708, 1995.
"Choy , et al., Safety and tolerability of duloxetine in the treatment of patients with fibromyalgia: pooled analysis of data from five clinical trials," Clin Rheumatol, 2009, vol. 28, pp. 1035-1044.
"Cousins , et al., The Role of Dopamine in Bipolar Disorder", Bipolar Disorders, vol. 11, pp. 787-806, 2009.
"Cuellar , et al., Distinctions Between Bipolar and Unipolar Depression", Clin. Psychol. Rev., vol. 25, No. 3, pp. 307-339, May 2005.
Damsma , et al., "Lack of tolerance to nicotine-induced dopamine release in the nucleus accumbens," European Journal of Pharmacology (1989) pp. 363-368.
Dl Chiara , et al., "Drugs abused by humans preferentially increase synaptic dopamine concentrations in the mesolimbic system of freely moving rats," Proc. National Academy of Science, USA, Jul. 1988, vol. 85, pp. 5274-5278.
Eyles , et al., "Oral Delivery and Fate of Poly(lactio acid) Microsphere-encapsulated Interferon in Rats", J. Pharm. Pharmacol, vol. 49, pp. 669-674, 1997.
Frye , et al., "Unmet Needs in Bipolar Depression", Depression and Anxiety, vol. 19, pp. 1999-208, 2004.
Fulda , et al., "Dopamine Agonists for the Treatment of Restless Legs Syndrome", Expert Opin. Pharmacother., vol. 6, No. 15, pp. 2655-2666, 2005.
Gao , et al., "Controlled Release of a Contraceptive Steroid from Biodegradable and Injectable Gel Formulations: In Vitro Evaluation", Pharmaceutical Research, vol. 12, No. 6, pp. 857-863, 1995.
Garcia-Borreguero , et al., "Circadian Variation in Neuroendocrine Response to L-dopa in Patients with Restless Legs Syndrome", Sleep, vol. 27, No. 4, pp. 669-673, 2004.
Garcia-Borreguero , et al., "Treatment of restless legs syndrome with gabapentin: A double-blind, cross-over study," Neurology, 59, Nov. 2002, p. 1573-1579.
Gendreau , et al., "Milnacipran is safe and well tolerated in the treatment of fibromyalgia syndrome," Abstract Only, 2008.
Gordon, R. , et al., "Pharmacological profile of YKP10A: a novel antidepressant", Abstracts of the annual meeting of the Society of Neuroscience, Jan. 1, 1998.
"Grund , et al., Behavioral and Brain Functions 2006,2:2,1-14,2006".
Harel , et al., "Effectiveness and Safety of Adjunctive Antidepressants in the Treatment of Bipolar Depression: A Review", Isr J Psychiatry Relat Sci, vol. 45, No. 2, pp. 121-128, 2008.

(56) References Cited

OTHER PUBLICATIONS

Hargreaves, et al., "A new and sensitive method for measuring thermal nociception in cutaneous hyperalgesia," Pain, 1988, vol. 32, pp. 77-88.

Harris, et al., "Newer treatments for fibromyalgia syndrome," Therapeutics and Clinical Risk Management, 2008, vol. 4, No. 6, pp. 1331-1342.

Hassan, et al., "How to Keep the Brain awake? The Complex Molecular Pharmacogenetics of Wake Promotion," Neuropsychopharmacology 34:1625-1640 (2009).

Hurt, et al., "A Comparison of Sustained-Release Bupropion and Placebo for Smoking Cessation." The New England Journal of Medicine Oct. 23, 1997, vol. 337, No. 17, pp. 1195-1202.

Imperato, et al., "Nicotine preferentially stimulates dopamine release in the limbic system of freely moving rats," European Journal of Pharmacology (1986) pp. 337-338.

Kessler, et al., "Lifetime Prevalence and Age-of-Onset Distributions of DSM-IV Disorders in the National Comorbidity Survey Replication", Arch Gen Psychiatry, vol. 62, pp. 593-602 & 768, Jun. 2005.

Kessler, et al., "Prevalence, Severity and Comorbidity of Twelve-month DSM-IV Disorders in the National Comorbidity Survey Replication (NCS-R)", Arch Gen Psychiatry, vol. 62, No. 6, pp. 617-627, Jun. 2005.

Kim, et al., "Bupropion May Improve Restless Legs Syndrome", Clin Neuropharmacol, vol. 28, No. 6, pp. 298-301, Nov.-Dec. 2005.

Kim, et al., "Pregabalin for fibromyalgia: Some relief but no cure," Cleveland Clinic Journal of Medicine, Apr. 2009, vol. 76, No. 4, pp. 255-261.

Miklowitz, et al., "The Psychopathology and Treatment of Bipolar Disorder", Annu. Rev. Clin. Psychol., vol. 2, 2006.

Miller, et al., "Assessment Tools for Adult Bipolar Disorder", Clin Psychol. (New York), vol. 16, No. 2, pp. 188-201, Jun. 1, 2009.

Minto, et al., "Pharmacokinetics and Pharmacodynamics of Nandrolone Esters in Oil Vehicle: Effects of Ester, Injection Site and Injection Volume", The Journal of Pharmacology and Experimental Therapeutics, vol. 281, No. 1, pp. 93-102, 1997.

Nisell, et al., "Infusion of Nicotine in the Ventral Tegmental Area or the Nucleus Accumbens of the Rat Differentially Affects Accumbal Dopamine Release," Pharmacology & Toxicology, (1994) pp. 348-352.

Nisell, et al., "Nicotine Dependence, Midbrain Dopamine Systems and Psychiatric Disorders," Pharmacology & Toxicology (1995) pp. 157-162.

Nisell, et al., "Systemic Nicotine-Induced Dopamine Release in the Rat Nucleus Accumbens is Regulated by Nicotinic Receptors in the Ventral Tegmental Area," SYNAPSE (1994) pp. 36-44.

Nunes, et al., "Journal of the American Medical Association (2004) American Medical Association, vol. 291, pp. 1887-1896".

Ostro, et al., "Use of Liposomes as Injectable-Drug Delivery Systems", American Journal of Hospital Pharmacy, vol. 46, pp. 1576-1587, Aug. 1989.

Pontieri, et al., "Effects of nicotine on the nucleus accumbens and similarity to those of addictive drugs," Letters of Nature, Jul. 18, 1996, vol. 382, pp. 255-257.

Rader, et al., "American Family Physician, vol. 79, No. 8, 657-665, 2009".

Rapoport, Stanley, 1., , et al., "Bipolar Disorder and Mechanisms of Action of Mood Stabilizers", Brain Research Reviews, vol. 61, pp. 185-209, 2009.

Rohatagi, et al., "Pharmacokinetic and Pharmacodynamic Evaluation of Triamcinolone Acetonide After Intravenous, Oral, and Inhaled Administration", J. Clin. Pharmacol., vol. 35, pp. 1187-1193, 1995.

"Spencer, et al., vol. 79, No. 8, 3-9, 2002".

Stiasny-Kolster, et al., "Static Mechanical Hyperalgesia Without Dynamic Tactile Allodynia in Patients with Restless Legs Syndrome", Brain, vol. 127, No. 4, pp. 773-782, 2004.

Verdu, et al., "Antidepressants for the Treatment of Chronic Pain," Drugs, 2008, vol. 68, No. 18, pp. 2611-2632.

Vieta, et al., "Evolving Trends in the Long-Term Treatment of Bipolar Disorder", The World Journal of Bioiogical Psychiatry, vol. 8, No. 1, pp. 4-11, 2007.

"Xu, et al., Biorganic and Medicinal Chemistry (2006) Elsevier, vol. 14, pp. 3285-3299".

METHODS FOR TREATING ATTENTION-DEFICIT/HYPERACTIVITY DISORDER

STATEMENT OF PRIORITY

This application is a continuation of and claims priority to U.S. application Ser. No. 16/225,893, filed Dec. 19, 2018, which is a continuation of and claims priority to U.S. application Ser. No. 15/605,278, filed May 25, 2017, now U.S. Pat. No. 10,202,335, which is a continuation of and claims priority to U.S. application Ser. No. 14/495,532, filed Sep. 24, 2014, now U.S. Pat. No. 9,663,455, which is a continuation of and claims priority to U.S. application Ser. No. 13/508,147, filed Jun. 13, 2012, now U.S. Pat. No. 8,895,609, which is a 35 U.S.C. § 371 national phase application of PCT Application No. PCT/KR2010/007698, filed Nov. 3, 2010, which claims the benefit of U.S. Provisional Application No. 61/258,780, filed Nov. 6, 2009. The entire content of each of these applications is incorporated herein by reference.

TECHNICAL FIELD

The present invention relates a method of treating attention-deficit/hyperactivity disorder (ADHD). More specifically, the present invention is directed to a method of using a carbamate compound alone or in combination with other medications, for the treatment of ADHD.

BACKGROUND ART

ADHD is a chronic developmental disorder characterized by issues associated with attention, inhibiting irrelevant and/or focusing too intensely on specific stimuli to the extent that this interferes with being productive at work or school. This disorder has been found to be present in 3 to 10% of children and 1 to 6% of adults and 50-66% of children continue to, be affected by ADHD issues into adulthood (Spencer et al., 2002; Daley, 2004). There is a high risk of cigarette smoking and substance abuse in children with ADHD. Children growing up with ADHD can face academic impairments, social dysfunction and poor self-esteem.

The Diagnostic and Statistical Manual (DSM) IV defines five subtypes: predominately hyperactive/impulsive where patients shows 6 or more hyperactive/impulsive symptoms and fewer than 6 inattentive symptoms; predominately inattentive typo with 6 or more inattentive symptoms and fewer than 6 hyperactive/impulsivity symptoms; ADHD combined with 6 or more hyperactive/impulsivity and inattentive symptoms; partial remission where patient previous met criteria but currently only displays some impairing symptoms; and ADHD not otherwise specified where full criteria at not currently met and it is unclear that criteria were met in the past (Murphy & Adler, 2004). Complications of diagnosis of especially adults include that there is no diagnostic test for ADHD, other comorbid conditions, clinical subjective judgment is needed to determine interference of least 2 areas of life and the establishment of childhood onset may not be possible. Conditions that can either mimic ADHD symptoms or are comorbid with ADHD include conduct disorder, oppositional defiant disorder, maim depressive disorder, anxiety disorder, bipolar disorder, learning disabilities and substance abuse (Spencer et al 2002; Daley, 2004).

There is no clearly defined single etiology of ADHD. The pathophysiology of ADHD may be impacted by genetics, prenatal and perinatal risk factors and neurobiological deficits. Cigarette and alcohol exposure increases the risk along, with a 75% genetic component (Spencer et al., 2002). Areas of the brain involved in attention including the prefrontal cortex where dopamine and norepinephrine receptors pre dominate have been documented to be smaller and less active in ADHD patients compared to control implicating the catecholamines, dopamine and norpinephrine (Spencer et al., 2002; Grund et al., 2006; Rader et al., 2009).

The treatment of ADHD has been primarily with stimulant medication including methylphenidate, dextroamphetamine and mixture of stimulants as first-line treatment (Rader et al., 2009). Stimulant medications do not necessarily last for 24 hours even with extent ed. release formulations. Thus, stimulants need to be taken 2 to 3 times daily leading to compliance issues (Daughton & Kratochvil, 2009). However, compliance is improved with the extended release formulations by reducing stigma of taking medication at school but side effects continue until later in the day and tend to be expensive. Stimulants have the potential, for abuse and may not be ideal for comorbid conditions including tic disorders (Spencer et al., 2002). In addition, there is a need to monitor children for the impact of stimulant medication on growth (Daley, 2004) and for blood pressure and heart rate changes (Daughton & Kratochvil, 2009). Other side effects include appetite suppression, weight loss, abdominal pain, headache, irritability, cardiovascular effects, insomnia, skin irritation and rash (Rader et al., 2009).

Nonstimulant treatments have also been effective with advantages of longer duration of use, less abuse potential and treatment of comorbid conditions over stimulant medications (Daley, 2004). Atomoxetine considered a second-line treatment, shows high selectivity for the presynaptic norepinephrine transporter and promise in children and adults with ADHD with long lasting therapeutic effects and less abuse potential (Rader et al 2009; Daughton & Kratochvil, 2009). However, the efficacy that atomoxetine achieved was not up to the level of the stimulants. In addition, efficacy onset is gradual and there is a risk of suicidal ideation, jaundice and potential interaction with CYP 2D6 substrates.

Third-line treatments include tricyclic antidepressants, bupropion, and alpha$_2$ agonists (Rader et al., 2009). Tricyclic antidepressants with actions on catecholamine reuptake have been prescribed for ADHD but TCA action is not selective and adverse effects include dry mouth, blood pressure changes, weight gain, cardiac conduction delays and constipation. Buproprion, antidepressant with dopamine and norpinephrine agonist effects, appears to be effective in ADHD but there is a higher risk of drug-induced seizures albeit at higher dose levels, previous history of seizures and eating disorder (Daley, 2004). Side effects of clonidine and guanfacine, alpha$_2$ agonists, are drowsiness, dizziness, dry mouth and orthostatic hypotension but these drugs are useful for patients with conduct disorder and help counteract insomnia and appetite suppression caused by stimulants (Rader et at, 2009). Selective serotonin reuptake inhibitors have been investigated for ADHD but demonstration of efficacy has not been promising (Spencer et at, 2002).

DISCLOSURE OF INVENTION

Technical Problem

Accordingly, there is a need in the treatment of ADHD that would improve efficacy in the treatment of hyperactivity/impulsivity and inattentive symptoms with greater compliance and lower adverse effect profile including abuse potential.

Solution to Problem

The present invention is directed to a method of treating ADHD comprising the administration of a therapeutically effective amount of a compound having structural Formula (1) or a pharmaceutically acceptable salt thereof, to a mammal in need of treatment:

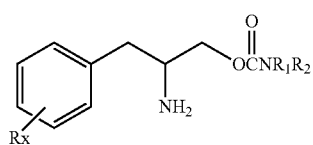

(1)

wherein,

R is selected from the group consisting of hydrogen, lower alkyl of 1 to 8 carbon atoms, halogen selected from F, Cl, Br and I, alkoxy of 1 to 3 carbon atoms, nitro group, hydroxy, trifluoromethyl, and thioalkoxy of to 3 carbon atoms;

x is an integer of 1 to 3, with the proviso that R may be the same or different when x is 2 or 3;

$R_1$ and $R_2$ can be the same or different from each other and are independently selected from the group consisting of hydrogen, lower alkyl of 1 to 8 carbon atoms, aryl, arylalkyl, cycloalkyl of 3 to 7 carbon atoms;

$R_1$ and $R_2$ can be joined to form a 5 to 7-membered heterocycle substituted with a member selected from the group consisting of hydrogen, alkyl, and aryl groups, wherein the heterocyclic compound comprises 1 to 2 nitrogen atoms and 0 to 1 oxygen atom, and the nitrogen atoms are not directly connected with each other or with the oxygen atom.

In another embodiment, the present invention provides a method of improving symptoms associated with ADHD in a subject, comprising the stop of the administration, to a subject in need of such treatment, or a therapeutically effective amount a compound of the Formula (1) or a pharmaceutically acceptable salt thereof.

In further embodiment, the present invention provides a method of ameliorating or eliminating effects of ADHD in a subject, comprising the step of the administration, to a subject in need of such treatment, of a therapeutically effective amount a compound of the Formula (I) or a pharmaceutically acceptable salt thereof.

In additional embodiment, the present invention is directed to pharmaceutical composition for treating ADHD comprising a therapeutically effective amount a compound of the Formula (1) or a pharmaceutically acceptable salt thereof.

In another embodiment, the present invention provides a pharmaceutical composition for improving symptoms associated with ADHD a subject, comprising a therapeutically effective amount a compound of the Formula (1) or a pharmaceutically acceptable salt thereof.

In further embodiment, the present invention provides a pharmaceutical composition for ameliorating or eliminating symptoms of ADHD in a subject, comprising a therapeutically effective amount a compound of the Formula (1) or a pharmaceutically acceptable salt thereof.

The compound having structural Formula (1) is an enantiomer substantially free of other enantiomers or an enantiomeric mixture wherein one enantiomer of the compound having structural Formula (1) predominates. One enantiomer predominates to the extent of about 90% or greater, and preferably about 98% or greater, The enantiomer is (S) or (L) enantiomer as represented by Structural Formula (1a) or (R) or (D) enantiomer, as represented by Structural Formula (1b):

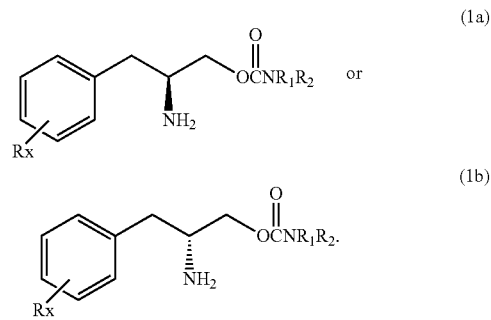

Preferably, Rx, $R_1$ and $R_2$ are all selected from hydrogen and x is 1, which are shown in the following formula:

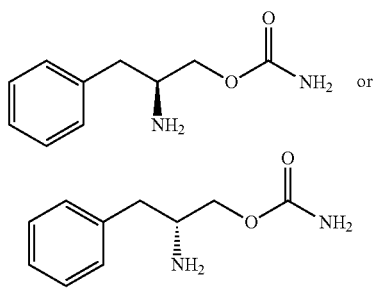

Embodiments of the invention include a method for using the enantiomer of Formula 1 substantially free of other enantiomers that is the enantiomer of Formula 1b or an enantiomeric mixture wherein the enantiomer of Formula 1b predominates. (Note: in the structural formula of Formula 1b below the amino group attached to the beta carbon projects into the plane of the paper. This is the dextrorotary (D) enantiomer that is of absolute configuration (R)).

Advantageous Effects of Invention

The present invention is based in part on the discovery that phenylalkylamino carbamates of Formula 1 discussed above have novel and unique pharmacological properties. These compounds have been shown in several animal models to have the ability to treat ADHD and modification of symptoms associated with ADHD.

Although the precise mechanism of action is not completely understood, it is known that these compounds do not work by the same mechanisms as most other known treatments for ADHD. For these reasons, the compounds of Formula 1 are especially suitable for use as sole or adjunctive treatment for ADHD and modification of symptoms associated with ADHD.

BEST MODE FOR CARRYING OUT THE INVENTION

Figure 1:
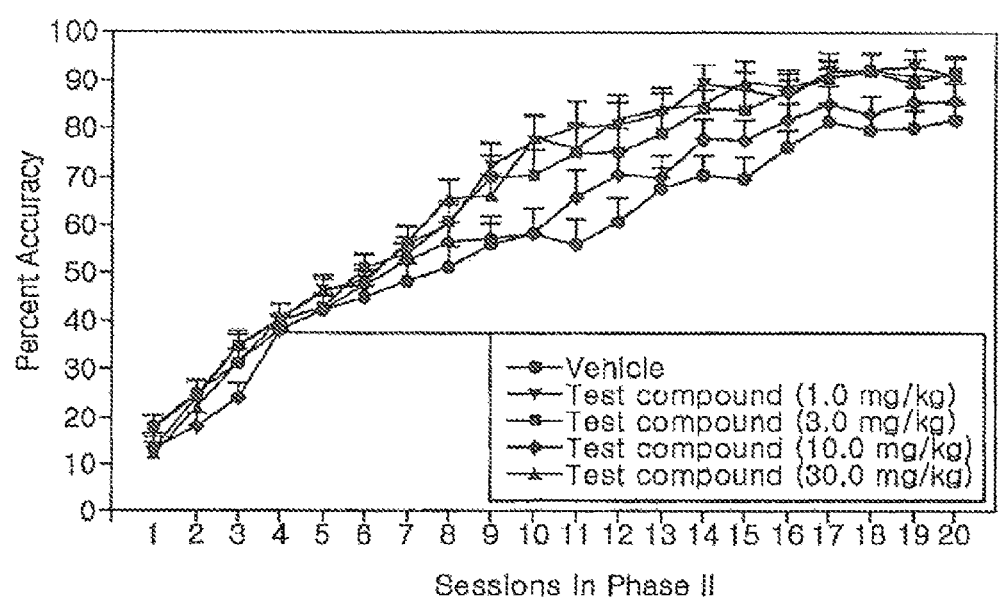
FIG. 1: Effect of Test Compound on Percent Accuracy During Phase II Reversal Training of a Visual Discrimination.

These and other objects of the invention will be more fully understood from the following description of the invention, the referenced drawings coached hereto and the claims appended hereto.

The present invention is directed to a method of treating ADHD comprising the administration of a therapeutically effective amount of a compound having structural Formula (1) or enantiomers, diastereomers, racemates or mixtures thereof, or hydrates, solvates and pharmaceutically acceptable salts and amides thereof, to a mammal in need of treatment:

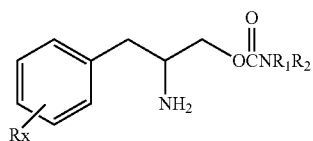

(1)

wherein,

R is selected from the group consisting of hydrogen, lower alkyl of 1 to 8 carbon atoms, halogen selected from F, Cl, Br and I, alkoxy of to 3 carbon atoms, nitro group, hydroxy, trithoromethyl, and thioalkoxy of 1 to 3 carbon atoms;

x is an integer of 1 to 3, with the proviso that R may be the same or different when x is 2 or 3;

$R_1$ and $R_2$ can be the same or different from each other and are independently selected from the group consisting of hydrogen, lower alkyl of 1 to 8 carbon atoms, aryl, arylalkyl, cycloalkyl of 3 to 7 carbon atoms;

$R_1$ and $R_2$ can be joined to form a 5 to 7-membered heterocycle substituted with a member selected from the group consisting of hydrogen, alkyl, and aryl groups, wherein the heterocyclic compound comprises 1 to 2 nitrogen atoms and 0 to 1 oxygen atom, and the nitrogen atoms are not directly connected with emit other or with the oxygen atom.

The present method also includes the use of a compound selected from the group consisting Formula 1a or 1b, or enantiomers, diastereomers, racemates or mixtures thereof, or hydrates, solvates and pharmaceutically acceptable salts and amides thereof:

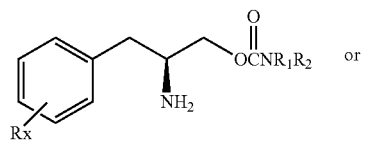

(1a)

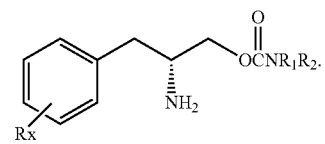

(1b)

wherein Rx, $R_1$ and $R_2$ are the same as defined above.

The present method also preferably includes the use of the D (or dextrorotary) enantiomer (of absolute configuration R) selected from the group consisting of Formula 1 or an enantiomeric mixture thereof. In the structural formula of Formula 1b, the amino group attached to the beta carbon projects into the plane of the paper. This is the dextrorotary (D) enantiomer that is of absolute configuration (R).

Preferably, in the Structural Formula 1, Rx, $R_1$ and $R_2$ are hydrogen and x is 1 as represented by following Structural Formula:

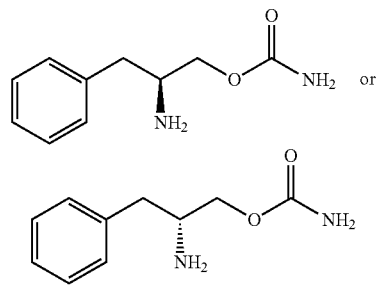

O-carbamoyl-(D)-phenylalaninol is also named (R)-(beta-amino-benzenepropyl) carbamate monohydrochloric acid. For enantiomeric mixtures, wherein O-carbamoyl-(D)-phenylalaninol predominates, preferably, to the extent of about 90% or greater, and more preferably about 98% or greater.

The compounds of Formula 1 can be synthesized by methods known to a skilled person in the art. Some reaction schemes for synthesizing compounds of Formula (1) have been described in published; U.S. Pat. Nos. 5,705,640, 5,756,817, 5,955,499, and 6,140,532. Details of the above reactions schemes as well as representative examples on the preparation of specific compounds have been described in published; U.S. Pat. Nos. 5,705,640, 5,750,817, 5,955,499, 6,140,532, all incorporated herein by reference in their entirety.

The salts of the compounds of Formula (1) can be produced by treating the compound with an acid (HX) in suitable solvent or by means well known to those of skill in the art.

From Structural Formula 1, it is evident that some of the compounds of the invention have at least one and possibly more asymmetric carbon atoms. It is intended that the present invention include within its scope the stereochemically pure isomeric forms of the compounds as well as their racernates. Stereochemically pure isomeric forms may be obtained by the application of art known principles. Diastereoisomers may be separated by physical separation methods such as fractional crystallization and chromatographic techniques, and enantiomers may be separated from each other by the selective crystallization of the diastereomeric salts, with optically active acids or bases or by chiral chromatography. Pure stereoisomers may also be prepared synthetically from appropriate stereochemically pure starting materials, or by using stereoselective reactions.

During any of the processes for preparation of the compounds of the present invention, it may be necessary and/or desirable to protect sensitive or reactive groups on my of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, Third Edition, John Wiley & Sons, 1999, The protecting groups may be removed at a convenient subsequent stage using methods known from the art.

The present invention is based in part on the discovery that phenylalkylamino carbamates of Formula 1 discussed above have novel and unique pharmacological properties. These compounds have been shown in several animal models to have the ability to treat ADHD and modification of symptoms associated with ADHD.

Although the precise mechanism of action is not completely understood, it is known that these compounds do not work by the same mechanisms as most other known treatments for ADHD. For these reasons, the compounds of Formula 1 are especially suitable for use as sole or adjunctive treatment for ADHD and modification of symptoms associated with ADHD.

Thus, these compounds can be safely used alone or in combination with other useful medications to provide enhanced efficacy and reduced side effects because smaller doses of each drug that could be used.

In one aspect, this invention relates to methods to treat subjects suffering from ADHD; the method comprising delivering to the subject a therapeutically effective amount of one or more of the carbamate compounds of the invention or a pharmaceutically acceptable salt thereof and a pharmaceutically acceptable carrier, diluent or excipient.

In another aspect, this invention also provides a method for diminishing, inhibiting or eliminating the symptoms of ADHD including hyperactivity/impulsivity and inattentive symptoms in a subject suffering from ADHD which comprises administering to the subject an effective amount of carbarnate compounds of the invention to diminish, inhibit or eliminate said symptoms.

Definitions

For convenience, certain terms employed in the specification, examples, and appended claims are collected here.

It is to be understood that this invention is not limited to the particular methodology, protocols, animal species or genera, and reagents described, as such may vary. It is also to be understood that the terminology used herein is for the purpose of describing particular embodiments only, and is not intended to limit the scope of the present invention that will be limited only by the appended claims.

As used herein the term "subject" refers to an animal, preferably a mammal, and most preferably a human both male and female, who has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of one or more of the signs or symptoms of the disease or disorder being treated.

The term "prophylactically effective amount" is intended to mean that amount of a pharmaceutical drug that will prevent at reduce the risk of occurrence of the biological or medical event that is sought to be prevented of a tissue, a system, animal or human that is being sought by a researcher, veterinarian, medical doctor or other clinician.

The term "pharmaceutically acceptable salts" shall mean non-toxic salts of the compounds employed in this invention which are generally prepared by reacting the free acid with a suitable organic or inorganic base. Examples of such salts include, but are not limited to, acetate, benzenesulfonate, benzoate, bicarbonate, bisulfate, bitartrate, borate, bromide, calcium, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, oleate, oxalate, parnaote, palmitate, panthothenate, phosphate/diphosphate, polygalacturonate, potassium, salicylate, sodium, stearate, subacetate, succinate, tannate, tartrate, teoclate, tosylate, triethiodide, valerate.

Therefore, the term "a patient in need of treatment" as used herein will refer to any subject or patient who currently has or may develop any of the above syndromes or disorders, including any mood disorder which can be treated by antidepressant medication, or any other disorder in which the patients present clinical condition or prognosis could benefit from the administration of one or more compounds of Formula (1) alone or in combination with another therapeutic intervention including but not limited to another medication.

The term "treating" or "treatment" as used herein, raters to any indicia of success in the prevention or amelioration of an injury, pathology or condition of ADHD and modification of symptoms of ADHD including any objective or subjective parameter such as abatement; remission; diminishing of symptoms or making the injury, pathology, or condition more tolerable to the patient; slowing in the rate of degeneration or decline or worsening of the illness; making the final point of worsening less debilitating; or improving, a subject's physical or mental well-being. The treatment or amelioration of symptoms can be based on objective or subjective parameters; including the results of a physical examination, neurological examination, and/or psychiatric evaluations. Accordingly, the term's "treating" or "treatment" includes the administration of the compounds or agents of the present invention for treatment of any form of ADHD in both males and females. In some instances, treatment with the compounds of the present invention will done in combination with other compounds to prevent, inhibit, or arrest the progression of the ADHD.

The term "therapeutic effect" as used herein, refers to the effective improvement in or reduction of symptoms of ADHD. The term "a therapeutically effective amount" as Used herein means a sufficient amount of one or more of the compounds of the invention to produce a therapeutic effect, as defined above, in a subject or patient in need of such ADHD treatment.

The terms "subject" or "patient" are used herein interchangeably and as used herein mean any mammal including but not limited to human beings including a human patient or subject to which the compositions of the invention can be administered. The term mammals include human patients, both male and female and non-human primates, as well as experimental animals such as rabbits, rats, and mice, and other animals.

Methods are known in the art for determining therapeutically and prophylactically effective doses far the Instant pharmaceutical composition. For example the compound can be employed at a daily dose in the range of about 0.1 mg to 400 mg usually on a regimen of 1 to 2 times per day, for an average adult human. The effective amount, however, may be varied depending upon the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

The compound may be administered to a subject by any conventional route of administration, including, but not limited to, intravenous, oral, subcutaneous, intramuscular, intradermal and parenteral. Depending on the route of administration, compounds of Formula (1) can be constituted into any form. For example, forms suitable for oral administration include solid forms, such as pills, gelcaps, tablets, caplets, capsules (each including immediate release, timed release and sustained release formulations), granules, and powders. Forms suitable for oral administration also include liquid forms, such as solutions, syrups, elixirs, emulsions, and suspensions. In addition, forms useful for parenteral administration include sterile solutions, emulsions and suspensions.

To prepare the pharmaceutical compositions of this invention, one or more compounds of formula (1) or salt thereof as the active ingredient is intimately admixed with a pharmaceutical carrier according to conventional pharmaceutical compounding techniques. Carriers are necessary and inert pharmaceutical excipients, including, but not limited to, binders, suspending agents, lubricants, flavorings, sweeteners, preservatives, dyes, and coatings. In preparing compositions in oral dosage form, any of the usual pharmaceutical carriers may be employed. For example, for liquid oral preparations, suitable carriers and additives include water, glycols, oils, alcohols, flavoring agents, preservatives, coloring agents and the like; for solid oral preparations, suitable carriers and additives include starches, sugars, diluents, granulating agents, lubricants, binders, disintegrating agents and the like. For parenteral use, the earlier will usually comprise sterile water, though other ingredients, for example, for purposes such as aiding solubility or for preservation, may be included. Injectable suspensions may also be prepared, in which case appropriate liquid carriers, suspending agents and the like may be employed.

Because of their ease in administration, tablets and capsules represent the most advantageous oral dosage unit form, in which case solid pharmaceutical carriers are obviously employed. If desired, tablets may be sugar coated or enteric coated by standard techniques. Suppositories may be prepared, in which case cocoa butter could be used as the carrier. The tablets or pills can be coated or otherwise compounded to provide a dosage form affording the advantage of prolonged action. For example, the tablet or pills can comprise an inner dosage and air outer dosage component, the latter being in the form of an envelope over the former. The two components can be separated by an enteric layer, which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The active drug can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidycholines.

Active drug may also be delivered by the use of monoclonal antibodies as individual carriers to which the compound molecules are coupled. Active drug may also in coupled with soluble polymers as targetable drug carriers. Such polymers can include polyvinyl-pyrrolidone, pyran copolymer, polyhydroxy-propyl-methacrylamide-phenol, polyhydroxy-ethyl-aspartamide-phenol, or polyethyleneoxide-polylysine substituted with palmitoyl residues. Furthermore, active drug may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels.

Preferably these compositions are in unit dosage forms such as tablets, pills, capsules, powders, grannies, sterile parenteral solutions or suspensions, metered aerosol or liquid sprays, drops, ampoules, auto-injector devices or suppositories, for oral parenteral, intranasal, sublingual or rectal administration, or for administration by inhalation or insufflation.

Alternatively the too position may be presented in a form suitable for one-weekly at once-monthly administration; for example, an insoluble salt of the active compound, such as the decanoate salt, may be adapted to provide a depot preparation for intramuscular injection.

The pharmaceutical compositions herein will contain, per dosage unit, e.g., tablet, capsule, powder, injection, teaspoonful, suppository and the like, an amount of the active ingredient necessary to deliver an effective dose as described above. For example, the pharmaceutical compositions herein can contain, per unit dosage unit, from about 25 to about 400 mg of the active ingredient. Preferably, the range is from about 50 to about 200 mg of the active ingredient.

In some embodiments of the present invention carbamate compounds suitable for use in the practice of this invention will be administered either singly or concomitantly with at least one or more other compounds or therapeutic agents. In these embodiments, the present invention provides methods to treat ADHD and modification of symptoms associated with ADHD in a patient. The method includes the step of administering to a patient in need of treatment, an effective amount of one of the carbamate compounds disclosed herein in combination with an effective amount of one or more other compounds or therapeutic agents.

It is understood that substituents and substitution patterns on the compounds of the present invention can be selected by one of ordinary skill in the art to provide compounds that are chemically stable, and that can be readily synthesized by techniques known in the art as well as the methods provided herein.

The present invention includes the use of isolated enantiomers of Formula 1. In one preferred embodiment, a pharmaceutical composition comprising the isolated S-enantiomer of Formula 1 is used to provide ADHD treatment in a subject. In another preferred embodiment, a pharmaceutical con position comprising the isolated R-enantiomer of Formula 1 is used to provide ADHD treatment a subject.

The present invention also includes the use of mixtures of enantiomers of Formula 1. In one aspect of the present invention, one enantiomer will predominate. An enantiomer that predominates in the mixture is one that is present in the mixture in an amount greater than any of the other enantiomers present in the mixture, e.g., in an amount greater than 50%. In one aspect, one enantiomer will predominate to the extent of 90% or to the extent of 91%, 92%, 93%, 94%, 95%, 96%, 97% or 98% or greater. In one preferred embodiment, the enantiomer that predominates in a composition comprising a compound of Formula 1 is the S-enantiomer of Formula 1.

The present invention provides methods of using enantiomers and enantiomeric mixtures of compounds represented by Formula 1. A carbamate enantiomer of Formula 1 contains a chiral center on the second aliphatic carbon adjacent to the phenyl ring.

An enantiomer that is isolated is one that is substantially free of the corresponding enantiomer. Thus, an isolated enantiomer refers to a compound that is separated via separation techniques or prepared free of the corresponding enantiomer. The term "substantially free", as used herein, means that the compound is made up of a significantly greater proportion of one enantiomer. In preferred embodiments, the compound includes at least about 90% by weight of a preferred enantiomer. In other embodiments of the invention, the compound includes at least about 99% by weight of a preferred enantiomer. Preferred enantiomers can be isolated from racemic mixtures by any method known to those skilled in the art, including high performance liquid chromatography (HPLC) and the formation and crystallization of chiral salts, or preferred enantiomers can be prepared by methods described herein.

Carbamate Compounds as Pharmaceuticals

The present invention provides racemic mixtures, enantiomeric mixtures and isolated enantiomers of Formula 1 as pharmaceuticals. The carbamate compounds are formulated as pharmaceuticals to provide anti-ADHD action in a subject.

In general, the carbamate compounds of the present invention can be administered as pharmaceutical compositions by any method known in the art for administering therapeutic drugs including oral, buccal, topical, systemic (e.g., transdermal, intranasal, or by suppository), or parenteral (e.g., intramuscular, subcutaneous, or intravenous injection.) Administration of the compounds directly to the nervous system can include, for example, administration to intracerebral, intraventricular, intacerebroventricular, intrathecal, intracisternal, intraspinal or peri-spinal routes of administration by delivery via intracranial or intravertebral needles or catheters with or without pump devices.

Compositions can take the form of tablets, pills, capsules, semisolids, powders, sustained release formulations, solutions, suspensions, emulsions, syrups, elixirs, aerosols, or any other appropriate, compositions and comprise at least one compound of this invention in combination with at least one pharmaceutically acceptable excipient. Suitable excipients are well known to persons of ordinary skill in the art, and they, and the methods of formulating the compositions, can be found in such standard references as Alfonso A R: Remington's Pharmaceutical Sciences, 17th ed., Mack Publishing Company, Easton, Pa., 1985, the disclosure of which is incorporated herein by reference in its entirety and for all purposes. Suitable carriers, especially for injectable solutions, include water, aqueous saline solution, aqueous dextrose solution, and glycols.

The carbamate compounds can be provided as aqueous suspensions. Aqueous suspensions of the invention can contain it carbamate compound in admixture with excipients suitable for the manufacture of aqueous suspensions. Such excipients can include, for example, a suspending agent, such as sodium carboxymethylcellulose, methylcellulose, hydroxypropylmethylcellulose, sodium alginate, polyvinylpyrrolidone, gum tragacanth and gum acacia, and dispersing or wetting agents such us a natural); occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptade-caethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate).

The aqueous suspension can also contain one or more preservatives such as ethyl or n-propyl p-hydroxybenzoate, one or more coloring agents, one or more flavoring agents, and one or more sweetening agents, such as, sucrose, aspartame or saccharin. Formulations can be adjusted for osmolarity.

Oil suspensions for use in the present methods can be formulated by suspending a carbamate compound in a vegetable oil, such as arachis oil, olive oil, sesame oil or coconut oil, or in a mineral oil such as liquid paraffin; or a mixture of these. The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. A an example of an injectable oil vehicle, see Minto, J. Pharmacol. Exp. Ther. 281:93-102, 1997. The pharmaceutical formulations of the invention can also be in the form of oil-in-water emulsions. The oily phase can be a vegetable oil or a mineral oil, described above, or a mixture of these.

Suitable emulsifying agents include naturally occurring gums, such as gum acacia, and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

The compound of choice, alone or in combination with other suitable components can be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations of the present invention suitable for parenteral administration, such as, for example, by intraarticular (in the joints), intravenous, intramuscular, intradermal, intraperitoneal, and subcutaneous tomes, can include aqueous and non-aqueous, isotonic sterile injection solutions, which can contain antioxidants, buffers, bacteriostats, and solutes that tender the formulation isotonic with the blood of the intended recipient, and aqueous and non-aqueous sterile suspensions that can include suspending agents, solubilizers, thickening agents, stabilizers, and preservatives. Among the acceptable vehicles and solvents that can be employed are water and Ringer's solution, an isotonic sodium chloride. In addition, sterile fixed oils can conventionally be employed as a solvent or suspending medium. For this purpose, any bland fixed oil can be employed including synthetic mono- or diglycerides. In addition, tatty acids such as oleic acid can likewise be used in the preparation of injectables. These solutions are sterile and generally free of undesirable matter.

Where the compounds are sufficiently soluble they can be dissolved directly in normal saline with or without the use of suitable organic solvents, such as propylene glycol or polyethylene glycol. Dispersions of the finely divided compounds can be made-up in aqueous starch or sodium carboxymethyl cellulose solution, or in suitable oil, such as arachis oil. These formulations can be sterilized by conventional, well-known sterilization techniques. The formulations can contain pharmaceutically acceptable auxiliary substances as required to approximate physiological conditions such as pH adjusting and buffering agents, toxicity adjusting agents e.g., sodium acetate, sodium chloride, potassium chloride, calcium chloride, sodium lactate and the like.

The concentration of a carbarnate compound in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated according to the known art using those suitable dispersing or wetting agents and suspending agents. The sterile injectable preparation can also be a sterile injectable solution or suspension in a nontoxic parenterally acceptable diluents or solvent, such as a solution of 1,3-butanediol. The formulations of commends can be presented in unit-dose or multi-dose sealed containers, such as ampoules and vials. Injection solutions and suspensions can be prepared from sterile powders, granules, and tablets of the kind previously described.

A carbamate compound suitable for use in the practice of this invention can be and is preferably administered orally. The amount of a compound of the present invention in the composition can vary widely depending on the type of composition, size of a unit dosage, kind of excipients, and other factors well known to those of ordinary skill in the art. In general, the final composition can comprise, for example, from 0.000001 percent by weight (% w) to 50% w of the carbamate compound, preferably 0.00001% w to 25% w, with the remainder being the excipient or excipients.

Pharmaceutical formulations for oral administration can be formulated using pharmaceutically acceptable carriers well known in the art in dosages suitable for oral administration. Such carriers enable the pharmaceutical formulations to be formulated in unit dosage, forms as tablets, pills, powder, dragees, capsules, liquids, lozenges, gels, syrups, slurries, suspensions, etc. suitable for ingestion by the patient.

Formulations suitable for oral administration can consist of (a) liquid solution, such as an effective amount of the pharmaceutical formulation suspended in a diluents, such as water, saline or polyethyleneglycol (PEG) 400 (b) capsules, sachets or tablets, each containing a predetermined amount, of the active ingredient, as liquids, granules or gelatin; (c) suspensions in an appropriate liquid; and (d) suitable emulsions.

Pharmaceutical preparations for oral use can be obtained through combination of the compounds of the present invention with a solid excipient, optionally grinding a resulting mixture, and processing the mixture of granules, after adding suitable additional compounds, if desired, to obtain tablets or dragee cores. Suitable solid excipients are carbohydrate or protein fillers and include, but are not limited to sugars, including lactose, sucrose, mannitol, sorbitol; starch from corn, wheat, rice, potato, or other plants; cellulose such as methyl cellulose, hydroxymethyl cellulose, hydroxypropylinethyl-cellulose or sodium carboxymethylcellulose; and gums including arabic and tragacanth as well as proteins such as gelatin and collagen.

If desired, disintegrating or solubilizing agents cart be added, such as the cross-linked polyvinyl pyrrolidone, agar, alginic acid, or a salt thereof, such as sodium alginate. Tablet forms can include one or more of lactose, sucrose, mannitol, sorbitol, calcium phosphates, corn starch, potato starch, microcrystalline cellulose, gelatin, colloidal silicon dioxide, tale, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

The compounds of the present invention can also be administered in the form of suppositories for rectal administration of the drug. These formulations can be prepared by mixing the drug with a suitable non-irritating excipient that is solid at ordinary temperatures but liquid at the rectal temperatures and will therefore melt in the rectum to release the drug. Such materials are cocoa butter and polyethylene glycols.

The compounds of the present invention can also be administered by intranasal, intraocular, intravaginal, and intrarectal routes including suppositories, insufflation, powders and aerosol formulations (for examples of steroid inhalants, see Rohatagi, J. Clin. Pharmacol, 35; 1187-1193, 1995; Tjwa, Ann. Allergy Asthma Immunol. 75:107-111, 1995).

The compounds of the present invention can be delivered transdermally, by a topical route, formulated as applicator sticks, solutions, suspensions, emulsions, gels, creams, ointments, pastes, jellies, paints, powders, and aerosols.

Encapsulating materials can, also be employed with the compounds of the present invention and the term "composition" can include the active ingredient in combination with an encapsulating material as a formulation, with or without other carriers. For example, the compounds of the present it can also be del send as microspheres for slow release in the body. In one embodiment, microspheres can be administered via intradermal injection of drag (e.g., mifepristone)-containing microspheres, which slowly release subcutaneously (see Rao, J. Biomater Sci. Polym. Ed. 7:623-645, 1995; as biodegradable and injectable gel formulations (see, e.g., Gao, Pharm. Res. 12:857-863, 1995); or, as microspheres for oral administration (see, e.g., Eyles, J. Pharm. Pharmacol. 49:669-674, 1997). Both transdermal and intradermal routes afford constant delivery for weeks or months. Cachets can also be used in the delivery of the compounds of the present invention.

In another embodiment, the compounds or the present invention can be delivered by the use of liposomes which fuse with the cellular membrane or are endocytosed, i.e., by employing ligands attached to the liposome that bind to surface membrane protein receptors of the cell resulting in endocytosis. By using liposomes, particularly where the liposome surface carries ligands specific for target cells, or are otherwise preferentially directed to a specific organ, one can focus the delivery of the carbamate compound into target cells in vivo. (See, e.g., Al-Muhammed, J. Microencapsul. 13:293-306, 1996; Chonn, Curr. Biotechnol. 6:698-708, 1995; Ostro, Am. J. Hosp, Pharm. 46:1576-1587, 1989).

The pharmaceutical formulations of the invention can be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation can be a lyophilized powder which can contain, for example, any or all of the following: 1 mM-50 mM histidine, 0.1%-2% sucrose, 2%-7% mannitol, a pH range of 4.5 to 5.5, that is combined with buffer prior to use.

Pharmaceutically acceptable salts refer to salts that are pharmaceutically acceptable and have the desired pharmacological properties. Such salts include salts that may be formed where acidic protons present in the compounds are capable of reacting with inorganic or organic bases. Suitable inorganic salts include those formed with the alkali metals, e.g. sodium and potassium, magnesium, calcium, and aluminum. Suitable Organic salts include those formed with organic bases such as the amine bases, e.g. ethanolamine diethanolamine, triethanolamine, tromethamine, N methylglucamine, and the like. Pharmaceutically acceptable salts can also include acid addition salts formed from the reaction of amine moieties in the patient compound with inorganic acids (e.g. hydrochloric and hydrobromic acids) and organic acids (e.g. acetic acid, citric acid, maleic acid, and the alkane- and arene-sulfonic acids such as methanesulfonic acid and benzenesulfonic acid). When there are two acidic groups present, a pharmaceutically acceptable salt may be a mono-acid-mono-salt or a di-salt; and similarly where there are more than two acidic groups present, some or all of such groups can be salified.

Compounds named in this invention can be present in unsalified form, or in salified form, and the naming of such compounds is intended to include both the original (unsalified) compound and its pharmaceutically acceptable salts. The present invention includes pharmaceutically acceptable salt forms of Formula (1). More than one crystal form of an enantiomer of Formula 1 can exist and as such are also included in the present invention.

A pharmaceutical composition of the invention can optionally contain, in addition to at carbamate compound, at least one other therapeutic agent useful in the treatment of ADHD. For example, the carbarnate compounds of Formula can be combined physically with other ADHD treatments in fixed dose combinations to simplify their administration.

Methods of formulating pharmaceutical compositions have been described in numerous publications such as Pharmaceutical Dosage Forms: Second Edition, Revised and Expanded, Volumes 1-3, edited by Lieberman et al; Pharmaceutical Dosage Forms: Parenteral Medications, Volumes 1-2, edited by Avis et al; and Pharmaceutical Dosage Forms: Disperse Systems. Volumes 1-2, edited by Lieberman et al; published by Marcel Dekker, Inc, the disclosure of which are herein incorporated by reference in their entireties and for all purposes.

The pharmaceutical compositions are generally formulated as sterile, substantially isotonic and in full compliance with all Good Manufacturing Practice (GMP) regulations of the U.S. Food and Drug Administration.

Dosage Regimens

The present invention provides methods of providing anti-ADHD action in a mammal using carbamate compounds. The amount of the carbamate compound necessary to reduce or treat ADHD is defined as a therapeutically or a pharmaceutically effective dose. The dosage schedule and amounts, effective for this use, i.e., the dosing or dosage regimen will depend on a variety of factors including the stage of the disease, the patient's physical status, age and the like. In calculating the dosage regimen for a patient, the mode of administration is also taken into account.

A person of ordinary skill in the art will be able without undue experimentation, having regard to that skill and this disclosure, to determine a therapeutically effective amount of a particular substituted carbamate compound for practice of this invention (see, e.g. Lieberman, Pharmaceutical Dosage Forms (Vols. 1-3, 1992); Lloyd, 1999. The art, Science and Technology of Pharmaceutical Compounding; and Pickar, 1999. Dosage Calculations). A therapeutically effective dime is also one in which any toxic or detrimental side effects of the active agent that is outweighed in clinical terms by therapeutically beneficial effects. It is to be further noted that for each particular subject, specific dosage regimens should be evaluated and adjusted over tune according to the individual need and professional judgment of the person administering or supervising the administration of the compounds.

For treatment purposes, the compositions or compounds disclosed herein can be administered to the subject in a single bolus delivery, via continuous delivery over an extended time period, or in a repeated administration, protocol (e.g., by an hourly, daily or weekly, repeated administration protocol). The pharmaceutical formulations of the present invention can be administered, for example, one or more times daily, 3 times per week, at weekly. In one embodiment of the present invention, the pharmaceutical formulations of the present invention are orally administered once or twice.

In this context, a therapeutically effective dosage of the carbamate compounds can include repeated doses within a prolonged treatment regimen that will yield clinically significant results to treat ADHD. Determination of effective dosages in this context is typically based on animal model studies followed up by human clinical trials and is guided by determining effective dosages and administration protocols that significantly reduce the occurrence or severity of targeted exposure symptoms or conditions in the subject. Suitable models in this regard include, for example, murine, rat, porcine, feline, non-human primate, and other accepted animal model subjects known in the art. Alternatively, effective dosages can be determined using in vitro models (e.g., immunologic and his histopathologic assays). Using such models, only ordinary calculations and adjustments are typically required to determine all appropriate concentration and dose to administer a therapeutically effective amount of the biologically active agent(s) (e.g., amounts that are intranasally effective, transdermally effective, intravenously effective, or intramuscularly effective to elicit a desired response).

In an exemplary embodiment of the present invention, unit dosage forms of the compounds are prepared for standard administration regimens. In this way, the composition can be subdivided readily into smaller doses at the physician's direction. For example, unit dosages can be made up in pocketed powders, vial or ampoules and preferably in capsule, or tablet form.

The active compound present in these unit dosage forms of the composition can be present in an amount of, for example, from about 10 mg to about one grain or more, for single or multiple daily administration, according to the particular need of the patient. By initiating the treatment regimen with it minimal daily dose of about one gram, the blood levels of the carbamate compounds can be used to determine whether a larger or smaller dose is indicated.

Effective administration of the carbarnate compounds of this invention can be administered, for example, at an oral or parenteral dose of from about 0.01 mg/kg/dose to about 150 mg/kg/dose. Preferably, administration will be from about 0.1 mg/kg/dose to about 25 mg/kg/dose, more preferably from about 0.2 to about 18 mg/kg/dose. Therefore, the therapeutically effective amount of the active ingredient contained per dosage unit as described herein can be, for example, from about 1 mg/day to about 7000 mg/day for a subject having, for example, an average weight of 70 kg.

The methods of this invention also provide for kits for use in providing treatment of ADHD. After a pharmaceutical composition comprising one or more carbamate compounds of this invention, with the possible addition of one or more other compounds of therapeutic benefit, has been formulated in a suitable carrier, it can be placed in an appropriate container and labeled for providing ADHD treatment. Additionally, another pharmaceutical comprising at least one other therapeutic agent useful in the ADHD treatment can be placed in the container as well and labeled for treatment of the indicated disease. Such labeling can include, for example, instructions concerning the amount, frequency and method of administration of each pharmaceutical.

Although the foregoing invention has been described in detail by way of example for purposes or clarity of understanding, it will be apparent to the artisan that certain changes and modifications are comprehended by the disclosure and may be practiced without undue experimentation within the scope of the appended claims, which are presented by way of illustration not limitation. The following examples me provided to illustrate specific aspects of the invention, and are not meant to be limitations.

A better understanding of the present invention may be obtained in light of the following examples that are set forth to illustrate, but are not to be construed to limit, the present invention.

MODE FOR THE INVENTION

Example 1

The test compound (O-carbamoyl-(D)-phenylalaninol) administered at 3, 10 or 10 mg/kg IP was examined in a behavioral experiment designed to assess behavioral performance on the reversal of a visual discrimination. Animals treated with the 3.0 or 30.0 mg/kg of test compound or with amphetamine needed fewer trials to reach criterion levels of performance and had better accuracy scores relative to rats treated with vehicle. Thus, test compound, at certain doses, does seem to enhance behavioral performance in this task similar to that achieved with d-amphetamine sulfate.

(Methods)

Forty adult male Long-Evans rats (Charles River Laboratories, Wilmington, Mass.) approximately 250 g at the start of training were used as subjects in this study. Each shipment of rats went through five-day isolation prior to introduction to the general population. Rats were allowed a minimum of one additional week acclimation before operant training began.

Test compound was dissolved in sterile 0.9% saline at 3.0, 10.0, and 30.0 mg/mL, D-amphetamine, the reference compound, was also dissolved in 0.9% sterile saline at 1.0 mg/mL of the amphetamine salt.

After operant training began, rats were housed individually. Access to food was restricted to 12-20 grams per day to maintain animals at 85-90% free feeding body weight (relative to non-restricted rats). Rats were never deprived of water and continued gain weight while in the study.

After animals reached the training criteria on Phase I of the study, they were designated to one of the treatment groups; groups were matched for performance (days to criterion per in Phase I. The study was a mixed design (dose levels×repeated training sessions). The five dose levels were 1, 3, and 10 mg/kg test compound, 0.9 percent saline (vehicle) and 1.0 mg/kg d-amphetamine sulfate (reference compound) all delivered intraperitoneal (IP) at 1.0 mL/kg.

Animals were trained in a set of 10 operant testing chambers (Med Associates) containing two retractable response levers on the front wall. There were two stimulus lights in the chamber, one situated over each lever. The food magazine is located between the two response levers on the front wall and food delivery is signaled with a magazine light. Retrieval of the food pellet is detected by a photosensor within the food magazine. Dim illumination of the chamber is provided by a houselight over the center of the front wall.

Initially animals were shaped to press a lever for food. During this phase, both levers were extended into the chamber and the animal was rewarded with a 45 mg pellet for pressing a lever. The use of a side bias is prevented by retracting a lever once it exceeds five presses beyond the number of presses on the opposite lever. After trace consecutive days with 100 lever presses subjects were moved to Phase I of the study. In this phase, animals had to learn to press the lever beneath the illuminated signal light. On each trial, one of the signal lights (randomly chosen) was illuminated for 1.0 sec prior to presentation of the levers (30.0 sec limited hold). After the levers extend into the chamber, a press on the proximal lever resulted in the delivery of a food pellet. A press on the distal lever resulted in a time out signaled by extinguishing the houselight tat 5.0 sec. After either a correct or incorrect press, or an omission, the levers were retracted for the duration of the variable inter-trial-interval (ITT; 5 s+/−2 s). After stable responding (two consecutive days better than 80% correct) was established in this phase, animals began training in the drug administration portion of the experiment (Phase II).

In Phase II, animals were divided into five groups matched on percent accuracy and number of trials to criterion. Animals in each group were dosed with one of three doses of test compound (3.0, 10.0, or 300 mg/kg, IP), amphetamine (1.0 mg/kg, IP), or with the vehicle (saline) one hour prior to behavioral training. In Phase II the discrimination was reversed from that of Phase I such that animals were now rewarded for pressing the lever distal to the cue light. Animals were dosed daily approximately 60 min prior to training. Training continued until ad animals achieved two consecutive days above 80% correct on the new discrimination.

Data were analyzed using SPSS 12.0 for Windows (SSPS Inc., Chicago, Ill.). A mixed between groups, repeated measures ANOVA was conducted cm response accuracy data. A simple one-way ANOVA was conducted on the trials to criteria data from Phase II.

(Results)

Response Accuracy. Test compound resulted in significantly better performance on the reversal of the visual discrimination as measured by the percent accuracy. A mixed design ANOVA revealed significant main effects of session ($F_{19,665}=365.50$, $p<0.001$) and group ($F_{4,35}=3.08$, $p=0.028$), but, more importantly there was a significant group by session interaction ($F_{76,665}=1.78$, $p=0.019$). Visual inspection of the graph (see FIG. 1) shows that the vehicle and 10.0 mg/kg dose of test compound were lower than the 3.0, and 30.0 dose of test compound and the 1.0 mg/kg dose of d-amphetamine.

Figure 2:
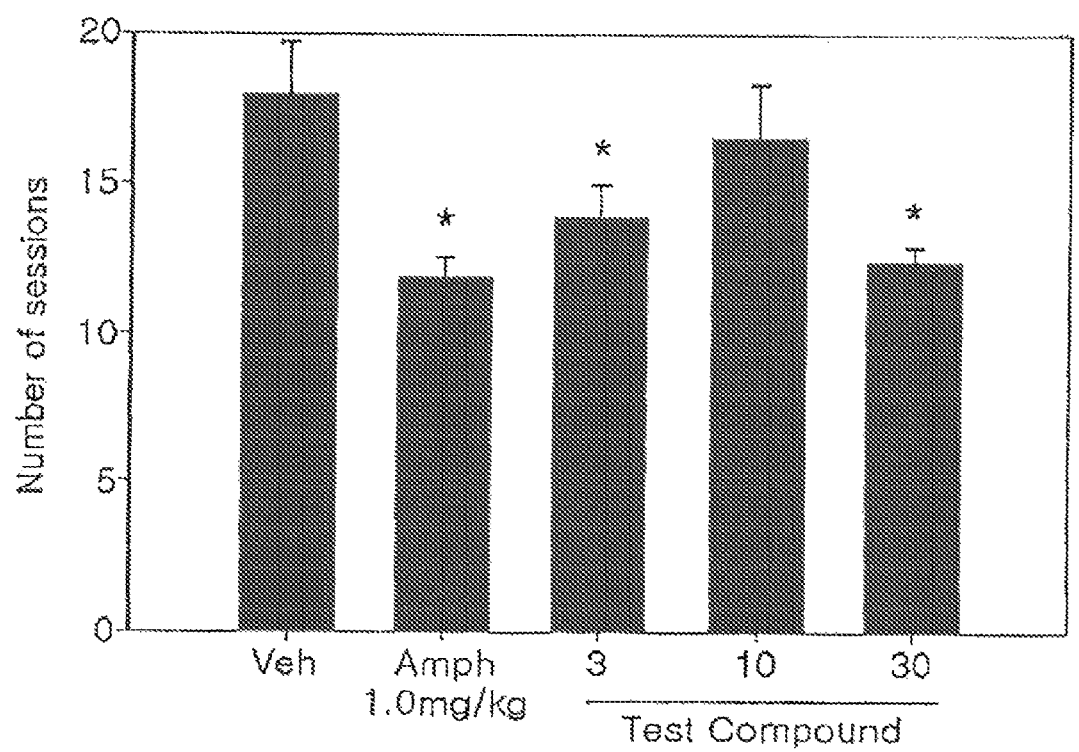
FIG. 2: Effect of Test Compound on the Number of Sessions Required to Reach Criteria in Phase II Reversal Training of a Visual Discrimination.

Sessions to criteria in Phase II. Test compound resulted in significantly better performance on the reversal of the visual discrimination as measured by the number of session required to reach criteria (see FIG. 2). A one-way ANOVA revealed an effect of session ($F_{4,35}=4.33$, $p=0.006$). Pairwise comparisons ($p<0.05$) confirm that more trials were required for the vehicle group to reach criterion levels of performance compared to the number of sessions required for animals that were dosed daily with 3.0, and 30.0 dose of test compound or the 1.0 mg/kg dose of d-amphetamine (note asterisks in FIG. 2). The group that was given 10.0 mg/kg of test compound did not differ from the vehicle group but was different from the 30 mg/kg dose of test compound and the d-amphetamine dosed groups. In FIG. 2, "*" denotes $p<0.05$ compared to vehicle control using LSD pairwise comparisons.

Example 2

The test compound administered at 10, 30 and 100 mg/kg subcutaneously (SC) was assessed to determine the influence on spontaneous activity of wild-type and homozygous mutant dopamine transporter knockout (KO) mice that bear some similarities to patients diagnosed with ADHD. The test compound selectively reduced activity of the KO mice in a dose-dependent manner suggesting that the test compound was high efficacious in depressing hyperactivity in dopamine transport KO mice.

(Methods)

Male and female wild-type and homozygous mutant dopamine transporter KO mice (n–10 mice/genotype/agent) were tested for spontaneous activity in the open field following a single injection of the vehicle or compound. Mice were placed into the open field for 30 min and administered SC the vehicle (sterile water) 2 mg/kg amphetamine, or three concentrations of the test compound (10, 30, 100 mg/kg). All drugs, were given in a volume of 5 mL/kg. Animals were returned to the open field for an additional 90 min. Spontaneous activity was evaluated in an automated Omnitech Digiscan apparatus (Accuscan Instruments, Columbus, Ohio). Activity was summated at 5 min intervals over the 2 h period of testing. Horizontal activity or locomotion was Measured in terms of toe total distance covered in cm, vertical activity or rearing was expressed in terms of the total numbers of vertical beam breaks, and stereotypy was quantified in terms of repetitive breaks of a given beam or beams with intervals of less than 1 sec. For the analyses, 10 WT and 10 KO mice were run in each of the treatment groups with approximately equal numbers of males and females assigned to each group. Data were analyzed by the Statistical Package for Social Sciences programs (version 11.0 for Windows; SPSS Science, Chicago, Ill.). The results lot each dependent variable were analyzed by repeated analyses of variance. (RMANOVA) for within subjects effects (group differences over time) and between-subjects effects (tests of main effects and interactions). Bonferroni corrected pair-wise comparisons were used as the post-hoc tests. A $p<0.05$ was considered significant.

(Results)

Baseline: KO mice showed higher levels of locomotor, rearing and stereotypical activities compared to WT mice.

Figure 3:
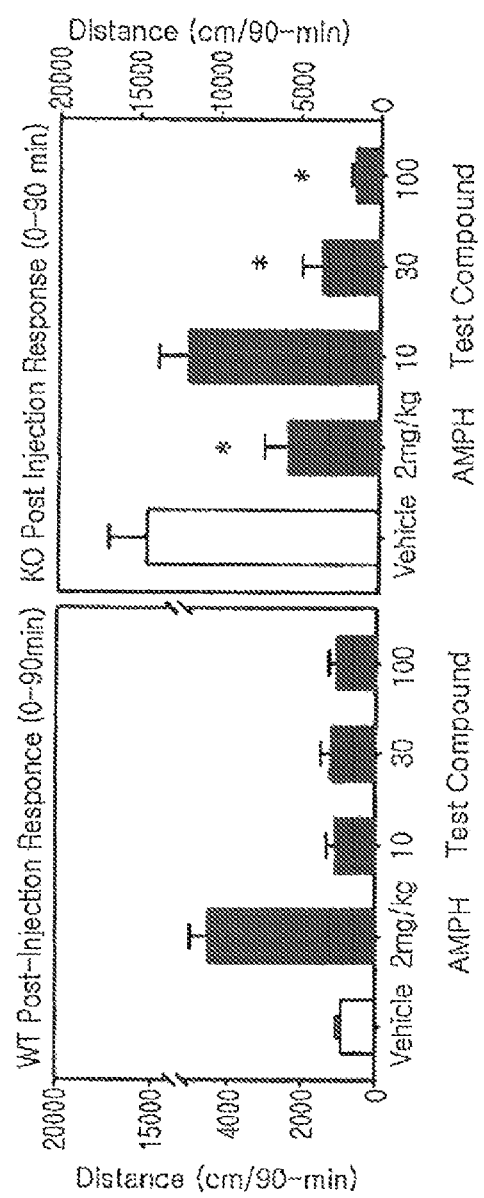
FIG. 3: Effect of Test Compound and Amphetamine a locomotor activity.

Drug Treatment: Amphetamine at 2 mg/kg SC increased locomotor, rearing and stereotypical activities in WY mice and decreased them in KO animals relative to the respective vehicle controls. The test compound reduced activities in a dose-dependent fashion and the 100 mg/kg dose suppressed activities more efficiently than amphetamine. Please see representative FIG. 3 for the locomotor activity (distance traveled in cm) collapsed over the 90 min post-injection period for Amphetamine (AMPH) and test compound. Rearing and stereotyped behavior showed similar results.

Example 3

The test compound was tested for binding to the dopamine, norepinephrine and serotonin transporters and for the effects on dopamine, norepinephrine and serotonin reuptake. The test compound showed weak binding to the dopamine and norepinephrine transporter and weak effects on dopamine and norepinephrine reuptake compared to cocaine.

(Methods)

Unknowns were weighed and dissolved in DMSO to make a 10 or 100 mM stock solution. An initial dilution to 50 or 500 µM in assay buffer for binding, or to 1 or 10 mM in assay buffer for uptake, was made. Subsequent dilutions were made with assay buffer supplemented with DMSO, maintaining a final concentration of 0.1% DMSO. Pipetting was conducted using a Biomek 2000 robotic workstation.

Concentrations of Test Compound Tested

Assay Concentration Range

Binding:

hDAT 21.6 nM-100 µM hSERT 21.6 nM-100 µM hNET 21.6 nm-10 µM

Uptake:

hDAT 31.6 nM-10 µM hSERT 31.6 nM-100 µM hNET 31.6 nM-100 µM

Inhibition of Radioligand Binding a [$^{125}$I]RTI-55 to hDAT, hSERT or hNET in Clonal Cells:

Cell preparation: HEK293 cells expressing hDAT, hSERT or hNET inserts are grown to 80% confluence on 150 mm diameter tissue culture dishes and serve as the tissue source. Cell membranes are prepared as follows. Medium is poured off the plate, and the plate is washed with 10 ml of calcium- and magnesium-free phosphate-buffered Lysis buffer (10 ml; 2 mM HEPES with 1 mM EDTA) is added. After 10 min, cells are scraped from plates, poured into centrifuge tubes, and centrifuged 30,000×g for 20 min. The supernatant fluid is removed, and the pellet is resuspended in 12-32 ml of 0.32 M sucrose using Polytron at setting 7 for 10 sec. The re-suspension volume depends on the density of binding sites within a cell line and is chosen to reflect binding of 10% or less of the total radioactivity.

Assay conditions: Each assay tube contains 50 µl of membrane preparation (about 10-15 µg of protein), 25 µl of unknown, compound used to define non-specific binding, or buffer (Krebs-HEPES, pH7.4; 122 mM NaCl, 2.5 mM CaCl2, 1.2 mM MgSO$_4$, 10 µM pargyline, 100 µM tropolone, 0.2% glucose, and 0.02% ascorbic acid, buffered with 25 mM HEPES), 25 µl [$^{125}$I]RTI-55 (40-80 pM final concentration) and additional buffer sufficient to bring up the final volume to 250 µl. Membranes are preincubated with unknowns for 10 min prior to the addition of the [$^{125}$I]RTI-55. The assay tribes are incubated at 25° C. for 90 min. Binding is terminated by filtration over GF/Cfilters, using a Tomtec 96-well cell harvester. Filters are washed for six seconds with ice-cold saline. Scintillation fluid is added to each square and radioactivity remaining on the filter is determined using a Wallac µ- or beta-plate reader. Specific binding is defined as the difference in binding observed in the presence mid absence of 5 µM mazindol (HEK-hDAT and HEK-hNET) or 5 µM imipramine (HEK-hSERT). Two or three independent competition experiments are conducted with duplicate determinations. GraphPAD Prism is used to analyze the ensuing data, with $IC_{50}$ values converted to $K_i$ values using the Cheng-Prusoff equation ($K_i=I_{50}/(1+([RTI-55]/K_d RTI-55))$).

Filtration Assay for Inhibition of [$^5$H]Neurotransmitter Uptake in HEK$_{293}$ Cells Expressing Recombinant Biogenic Amine Transporters:

Cell preparation: Cells are grown to confluence as described above. The medium is removed, and cells are washed twice with phosphate buffered saline (PBS) at room temperature. Following the addition of 3 ml Krebs-HEPES buffer, the plates are warmed in a 25° C. water bath for 5 min. The cells are gently scraped and then triturated with a pipette. Cells from multiple plates are combined. One plate provides enough cells for 48 wells, which is required to generate data on two complete curves for the unknowns.

Uptake inhibition assay conditions: The assay is conducted in 96 1-ml vials. Krebs HEPES (350 µl) and unknowns, compounds used to define non-specific uptake, or buffer (50 µl) are added to vials and placed in a 25° C. water bath. Specific uptake is defined as the difference in uptake observed in the presence and absence of 5 µM mazindol (HEK-hDAT and HEK-hNET) or 5 µM imipramine (HEK-hSERT). Cells (50 µl) are added and preincubated with the unknowns for 10 min. The assay is initiated by the addition of [$^3$H]dopamine, [$^3$H]serotonin, or [$^3$H]norepinephrine (50 µl, 20 nM final concentration). Filtration through Whatman GF/Cfilters presoaked in 0.05% polyethylenimine is used to terminate uptake after 10 min. The $IC_{50}$s are calculated applying the GraphPAD Prism program to triplicate curves made up of 6 drug concentrations each. Two or three independent determinations of each curve are made.

(Results)

The test compound was tested for its effects on radioligand ([$^{125}$I]RTI-55) binding to and [$^3$H]dopamine uptake by HEK cells expressing eDNA for the human dopamine transporter (HEX-hDAT cells), its effects on radioligand ([$^{125}$I]RTI-55) binding and [$^3$H]serotonin uptake by HEK cells expressing eDNA for the human serotonin transporter (HEK-hSERT cells), and its effects on radioligand ([$^{125}$I]RTI-55) binding and [$^3$H]norepinephrine uptake by HEX cells expressing eDNA for the human flare norepinephrine transporter (HEK-hNET cells).

In HEK-hDAT cells, the affinity of the compound for the binding site was lower than the affinity of cocaine, the standard compound, for the same site(s). The $K_i$ value for the displacement of [$^{125}$I]RTI-55 by the test compound was 14,200 nM, and the $K_i$ value for cocaine displacement of [$^{125}$H]RTI-55 binding was 236 nM. In the uptake assays test compound was less potent at blocking the uptake of [$^3$H]dopamine, with an $IC_{50}$ value of 2900 nM, as compared to the potency of cocaine ($IC_{50}$=385 nM). A Hill coefficient other than one suggests complex interactions with binding or uptake sites (Table 1).

In HEK-hSERT cells, the affinity of the compound for the binding site was lower than the affinity of cocaine, the standard compound, for the same site(s). The $K_i$ value for the displacement of [$^{125}$I]RTI-55 by test compound was 81,500 nM, and the $K_i$ value for cocaine displacement of [$^{125}$I]RTI-55 binding was 361 nM. In the uptake assays 31,827 was less potent at blocking the uptake of [3H]serotonin, with an $IC_{50}$ value greater than 100 µM, as compared to the potency of cocaine ($IC_{50}$=355 nM) (Table 2).

In HEK-hNET cells, the affinity of the compound for the binding site was lower than the affinity of cocaine, the standard compound, for the same site(s). The $K_i$ value for the displacement of [$^{125}$I]RTI-55 test compound was 3700 nM, and the $K_i$ value for cocaine displacement of [$^{125}$I]RTI-55 binding was 505 nM. In the uptake assays test compound was less potent at blocking the uptake of [$^3$H]norepinephrine, with an $IC_{50}$ value of 4400 nM, as compared to the potency of cocaine ($IC_{50}$=194 nM) (Table 3).

TABLE 1

| HEK-hDAT cells | Test Compound | Cocaine |
|---|---|---|
| [$^{125}$I]RTI-55 Binding $K_i$ (nM) | 14,200 ± 3,500 | 236 ± 58 |
| Hill coefficient | −0.77 ± 0.12 | −0.83 ± 0.04 |
| [$^3$H]Dopamine Uptake $IC_{50}$ (nM) | 2900 ± 920 | 385 ± 54 |

TABLE 2

Effects of test compound on HEK-hSERT

| HEK-hSERT cells | Test Compound | Cocaine |
|---|---|---|
| [$^{125}$I]RTI-55 Binding $K_i$ (nM) | 81.500 ± 2,900 | 361 ± 65 |
| Hill coefficient | −2.28 ± 0.05 | −0.77 ± 0.04 |
| [$^3$H]Serotonin Uptake $IC_{50}$ (nM) | >100 µM | 355 ± 39 |

TABLE 3

Effects of test compound on HEK-hNET cells

| HEK-hNET cells | Test Compound | Cocaine |
|---|---|---|
| [$^{125}$I]RTI-55 Binding $K_i$ (nM) | 3700 ± 1000 | 505 ± 67 |
| Hill coefficient | −1.45 ± 0.34 | −0.67 ± 0.07 |
| [$^3$H]NE Uptake $IC_{50}$ (nM) | 4400 ± 1100 | 194 ± 29 |

Numbers represent the means SEM from at least three independent experiments, each conducted with duplicate (for binding assays) or triplicate (for uptake assays) determinations. When the $K_i$ or the $IC_{50}$ for the test compound is greater than 10 µM, only two experiments are conducted and no standard error is reported.

Example 4

The test compound was tested for effects on extracellular monoaminergic transmitter levels, sampled via in vivo brain microdialysis in prefrontal cortical and striatal brain areas of freely-moving, conscious rats. Administration of the test compound at 30 mg/kg resulted in increased striatal dopamine and prefrontal norepinephrine.

(Methods)

Brain dialysates were collected from male Sprague-Dawey rats, which had been chronically implanted with cortical and striatal microdialysis guide cannulae and probes. The effects of different doses of test compound (10 and 30 mg/kg, administered subcutaneously) or vehicle (saline, 0.9% NaCl) were evaluated in three 50 baseline samples and eight consecutive 50 minute post-administration samples. The levels of dopamine, norepinephrine and serotonin for the two different brain areas were analyzed using HPLC/PCD analysis to determine any effects of the compound.

(Results)

Test compound at a dose of 10 mg/kg had no consistent effect on extracellular neurotransmitter levels in either brain region tested. At a dose of 30 mg/kg only, test compound caused increases in striatal dopamine and prefrontal cortical norepinephrine of rather variable magnitude, without having any significant affect on the other transmitters investigated.

Figure 4:
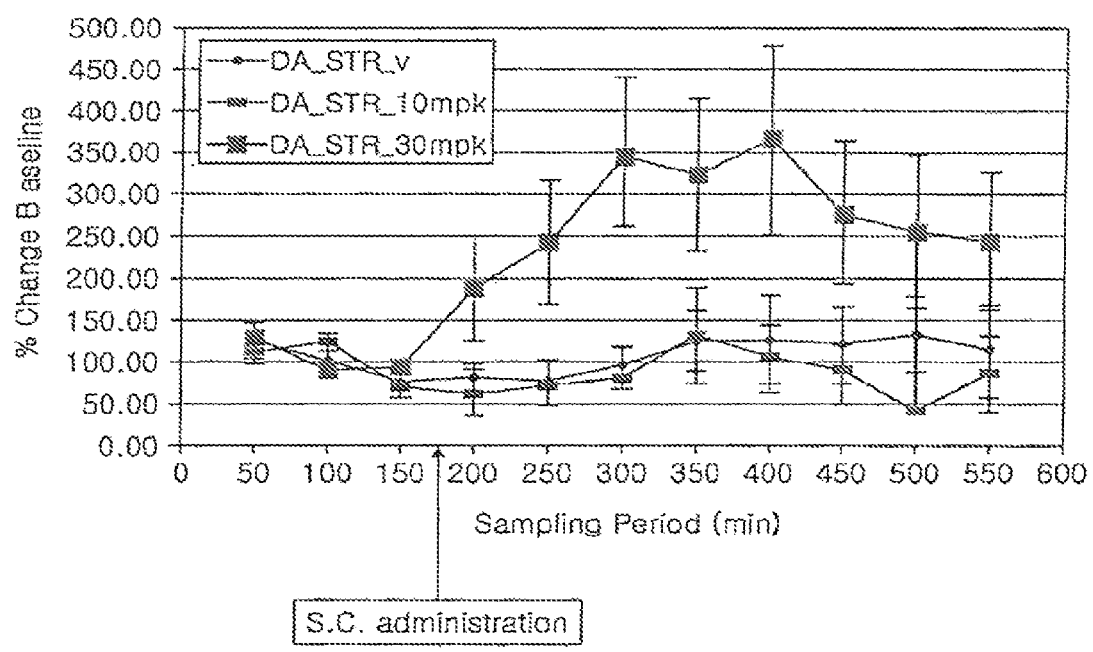
FIG. 4: Effects of administration of Test Compound or vehicle on extracellular dopamine concentrations in the striatum of rats.
Figure 5:
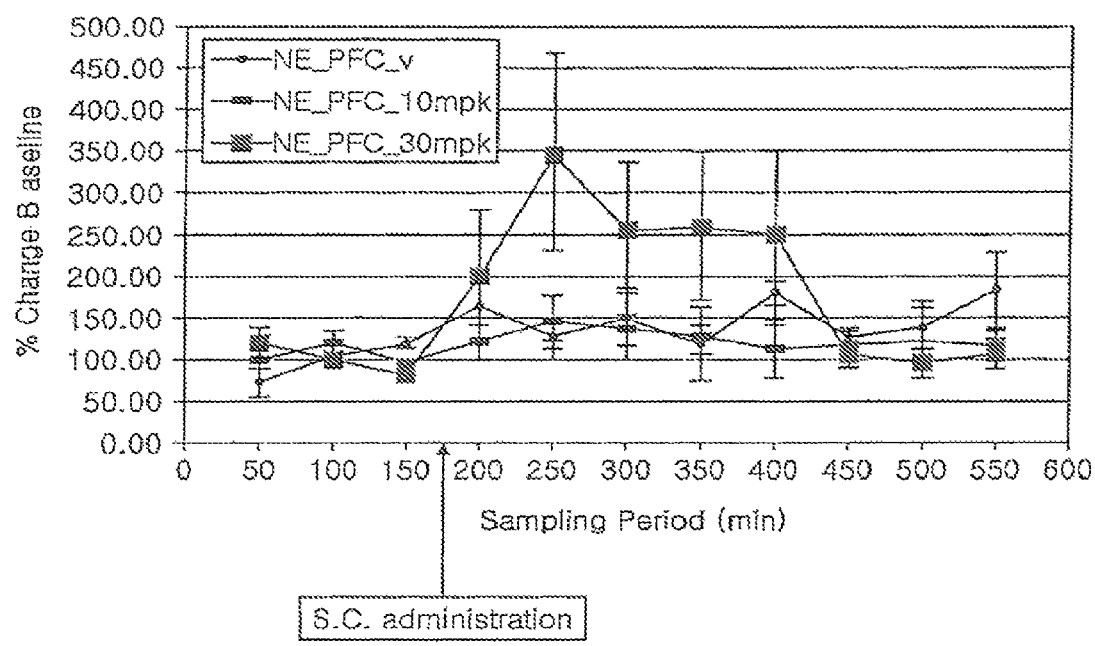
FIG. 5: Effects of administration of Test Compound or vehicle on extracellular norepinephrine concentrations in the prefrontal cortex of rats.

FIG. 4 shows effects of administration of Test Compound (10 and 30 mg/kg s.c.) or vehicle (0.9% NaCl) on extracellular dopamine concentrations in the striatum of rats during 3 baseline samples and 8 consecutive post-administration samples, and FIG. 5 shows effects of administration of Test Compound (10 and 30 mg/kg s.c.) or vehicle (0.9% NaCl) on extracellular norepinephrine concentrations in the prefrontal cortex of rats during 3 baseline samples and 8 consecutive post-administration samples.

In FIGS. 4 and 5, results are expressed as the average percentage change compared to the individual's average baseline value. The arrow indicates the time of administration of test compound. The average value (and corresponding S.E.M.) are shown for each 50 minute sample period of n=12 rats for each group (NB: individual data points may be based on fewer samples owing to incidental loss of dialysate samples).

References Cited

All references cited herein are incorporated herein by reference in their entirety and to all purposes to the carne extent as if cads individual publication or patent or patent application was specifically and individually indicated to be incorporated by reference in its entirety for all purposes.

The discussion of references herein is intended merely to summarize the assertions made by their authors and no admission is made that any reference constitutes prior at Applicants reserve the right to challenge the accuracy and pertinence of the cited references.

The present invention is not to be limited in terms of the particular embodiments described in this application, which are intended as single illustrations of individual aspects of the invention. Many modifications and variations of this invention can be made without departing from its spirit and scope, as will be apparent to those skilled in the art. Functionally equivalent methods and apparatus within the scope of the invention, in addition to those enumerated herein will be apparent to those skilled in the art from the foregoing description and accompanying drawings. Such modifications and variations are intended to fall within the scope of the appended claims. The present invention is to be limited only by the terms of the appended claims, along with the full scope of equivalents to which such claims are entitled.

The invention claimed is:

1. A method of treating ADHD, comprising the administration of a therapeutically effective amount of a compound having structural Formula (1) or a pharmaceutically acceptable salt thereof, to a mammal in need of treatment:

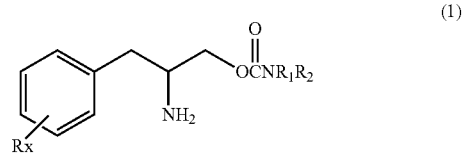

wherein

R is selected from the group consisting of hydrogen, lower alkyl of 1 to 8 carbon atoms, halogen selected from F, Cl, Br and I, alkoxy containing 1 to 3 carbon atoms, nitro group, hydroxy, trifluoromethyl, and thioalkoxy containing 1 to 3 carbon atoms;

x is an integer of 1 to 3, with the proviso that R may be the same or different when x is 2 or 3;

$R_1$ and $R_2$ can be the same or different from each other and are independently selected from the group consisting of hydrogen, lower alkyl of 1 to 8 carbon atoms, aryl, arylalkyl, cycloalkyl of 3 to 7 carbon atoms;

$R_1$ and $R_2$ can be joined to form a 5 to 7-membered heterocycle substituted with a member selected from the group consisting of hydrogen, alkyl, and aryl groups, wherein the heterocyclic compound comprises 1 to 2 nitrogen atoms and 0 to 1 oxygen atom, wherein the nitrogen atoms are not directly connected with each other or with the oxygen atom.

2. The method of claim 1, wherein R is hydrogen and x=1.

3. The method of claim 1, wherein R, $R_1$ and $R_2$ are hydrogen and x=1.

4. The method of claim 1, wherein the compound having structural Formula (1) is an enantiomer substantially free of other enantiomers or an enantiomeric mixture wherein one enantiomer of the compound having structural Formula (1) predominates.

5. The method of claim 4, wherein one enantiomer predominates to the extent of about 90% or greater.

6. The method of claim 5, wherein one enantiomer predominates to the extent of about 98% or greater.

7. The method of claim 4, wherein the enantiomer is (S) or (L) enantiomer as represented by Structural Formula (1a):

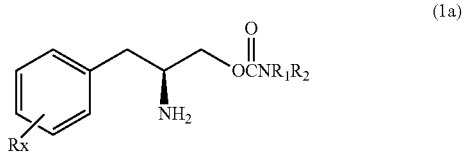

wherein R, x, $R_1$ and $R_2$ are as previously defined.

8. The method of claim 7, wherein one enantiomer predominates to the extent of about 90% or greater.

9. The method of claim 8, wherein one enantiomer predominates to the extent of about 98% or greater.

10. The method of claim 7, wherein Rx, $R_1$ and $R_2$ are hydrogen and x=1.

11. The method of claim 4, wherein the enantiomer is (R) or (D) enantiomer, as represented by Structural Formula (1b):

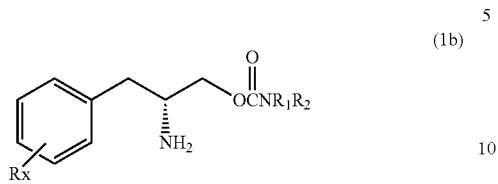

(1b)

wherein R, x, $R_1$ and $R_2$ are as previously defined.

12. The method of claim 11, wherein one enantiomer predominates to the extent of about 90% or greater.

13. The method of claim 12, wherein one enantiomer predominates to the extent of about 98% or greater.

14. The method of claim 11, wherein the enantiomer is (R)-(beta-amino-benzenepropyl) carbamate.

15. The method of claim 14, wherein the enantiomer of (R)-(beta-amino-benzenepropyl) carbamate predominates to the extent of about 90% or greater.

16. The method of claim 15, wherein the enantiomer of (R)-(beta-amino-benzenepropyl) carbamate predominates to the extent of about 98% or greater.

* * * * *

UNITED STATES PATENT AND TRADEMARK OFFICE
CERTIFICATE OF CORRECTION

PATENT NO. : 11,524,935 B2
APPLICATION NO. : 17/029151
DATED : December 13, 2022
INVENTOR(S) : Lee et al.

It is certified that error appears in the above-identified patent and that said Letters Patent is hereby corrected as shown below:

In the Specification

Column 2, Line 15: Please correct "extent ed." to read --extended--

Column 3, Line 51: Please correct "Formula (I)" to read --Formula 1--

Column 5, Line 46: Please correct "alkoxy of to 3" to read --alkoxy of 1 to 3--

Column 6, Line 54: Please correct "5,750,817" to read --5,756,817--

Column 13, Line 63: Please correct "400 (b)" to read --400; (b)--

Column 15, Lines 55-56: Please correct "Formula can" to read --Formula 1 can--

Column 19, Line 8: Please correct "365.50" to read --365.60--

Column 20, Line 10: Please correct "WY mice" to read --WT mice--

Column 21, Line 18: Please correct "$K_i=I_{50}/$" to read --$K_i=IC_{50}/$--

Column 21, Line 21: Please correct "$HEK_{293}$" to read --HEK293--

Column 21, Line 65: Please correct "$[^{125}H]$" to read --$[^{125}I]$--

Column 22, Line 8: Please correct "$[^{125}]$" to read --$[^{125}I]$--

Column 23, Line 8: Please correct "HPLC/PCD" to read --HPLC/ECD--

Signed and Sealed this
Twenty-first Day of March, 2023

Katherine Kelly Vidal
*Director of the United States Patent and Trademark Office*